(12) United States Patent
Jolly et al.

(10) Patent No.: US 8,591,544 B2
(45) Date of Patent: Nov. 26, 2013

(54) SUTURE LOOP CONSTRUCT WITH FREE FLOATING NEEDLE AND METHOD OF SURGERY

(75) Inventors: Jacob Jolly, Naples, FL (US); Matthew C. Summitt, Oviedo, FL (US)

(73) Assignee: Arthrex, Inc., Naples, FL (US)

(*) Notice: Subject to any disclaimer, the term of this patent is extended or adjusted under 35 U.S.C. 154(b) by 1040 days.

(21) Appl. No.: 11/882,306

(22) Filed: Jul. 31, 2007

(65) Prior Publication Data

US 2008/0027485 A1 Jan. 31, 2008

Related U.S. Application Data

(60) Provisional application No. 60/834,191, filed on Jul. 31, 2006.

(51) Int. Cl.
*A61B 17/06* (2006.01)
*A61F 2/08* (2006.01)

(52) U.S. Cl.
USPC ............................. 606/224; 600/36; 623/13.2

(58) Field of Classification Search
USPC .................. 606/222–232, 139, 144, 145, 148; 623/13.11, 13.12, 13.2; 128/898; 223/102; 600/36
See application file for complete search history.

(56) References Cited

U.S. PATENT DOCUMENTS

| | | | | |
|---|---|---|---|---|
| 1,293,660 A | * | 2/1919 | Armstrong | 223/102 |
| 2,715,486 A | * | 8/1955 | Marcoff-Moghadam et al. | 223/102 |
| 4,455,690 A | * | 6/1984 | Homsy | 623/13.15 |
| 4,667,860 A | * | 5/1987 | Feuerman | 223/99 |
| 4,950,285 A | * | 8/1990 | Wilk | 606/151 |
| 4,971,075 A | * | 11/1990 | Lee | 128/898 |
| 4,981,149 A | * | 1/1991 | Yoon et al. | 128/898 |
| 5,219,358 A | * | 6/1993 | Bendel et al. | 606/222 |
| 5,259,846 A | * | 11/1993 | Granger et al. | 606/224 |
| 5,643,295 A | * | 7/1997 | Yoon | 606/232 |
| 5,782,864 A | * | 7/1998 | Lizardi | 606/232 |
| 5,891,168 A | * | 4/1999 | Thal | 606/232 |
| 5,968,077 A | * | 10/1999 | Wojciechowicz et al. | 606/228 |
| 6,143,017 A | * | 11/2000 | Thal | 606/232 |
| 6,506,197 B1 | | 1/2003 | Rollero et al. | |
| 6,712,830 B2 | * | 3/2004 | Esplin | 606/152 |
| 6,716,234 B2 | | 4/2004 | Grafton et al. | |
| 2002/0019670 A1 | * | 2/2002 | Crawley et al. | 623/11.11 |
| 2004/0267316 A1 | | 12/2004 | Powell et al. | |
| 2007/0135843 A1 | | 6/2007 | Burkhart | |

FOREIGN PATENT DOCUMENTS

| | | |
|---|---|---|
| EP | 0 494 636 | 7/1992 |
| EP | 0 529 675 | 3/1993 |
| EP | 1 168 967 | 9/2002 |
| WO | WO 96/22735 | 8/1996 |
| WO | WO 00/54666 | 9/2000 |

* cited by examiner

*Primary Examiner* — Corrine M McDermott
*Assistant Examiner* — Christopher L Templeton
(74) *Attorney, Agent, or Firm* — Dickstein Shapiro LLP

(57) ABSTRACT

A system and method for tissue repair employing a continuous loop of suture attached to a free floating needle. The free floating needle is not swaged on the suture so that, after passing the suture loop construct through the tissue to be treated, the needle may be recentered if the suture strands are uneven.

2 Claims, 4 Drawing Sheets

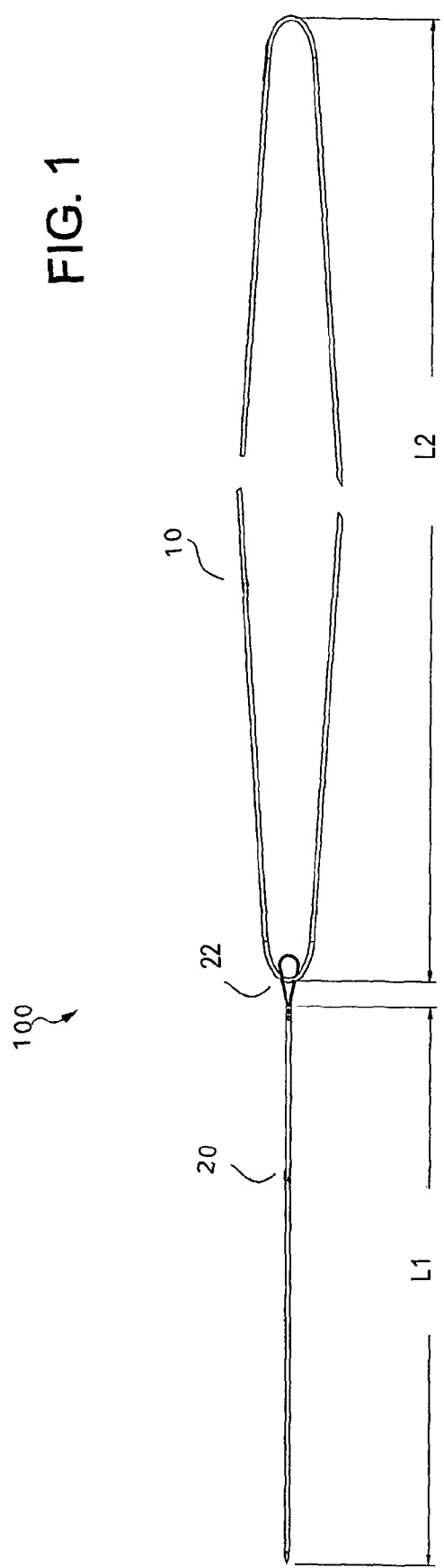

SUTURE LOOP CONSTRUCT WITH FREE FLOATING NEEDLE AND METHOD OF SURGERY

CROSS-REFERENCE TO RELATED APPLICATIONS

This application claims the benefit of U.S. Provisional Application Ser. No. 60/834,191, filed on Jul. 31, 2006, the entire disclosure of which is incorporated by reference herein.

FIELD OF THE INVENTION

The present invention relates to a continuous loop of suture attached to a free floating needle and having increased strength characteristics. The invention also relates to a method of surgery using a continuous loop of suture with a free floating needle for treatment of tissue.

BACKGROUND OF THE INVENTION

When soft tissue tears away from bone, reattachment becomes necessary. Various fixation devices, including sutures, screws, staples, wedges, and plugs have been used in the past to secure soft tissue to bone. More recently, various types of suture strands have been developed.

Suture strength is an important consideration in any surgical suture material. One of the strongest materials currently formed into elongated strands is an ultrahigh molecular long chain weight polyethylene, typically used for fishing line and the like, which is sold under the trade names DYNEEMA or SPECTRA.

Improved suture/needle constructs and methods of threading suture through tissue, or around tissue, with maximum suture fixation strength, as well as methods of securing tissue to tissue that allow for accelerated tissue healing are needed.

SUMMARY OF THE INVENTION

The present invention provides a system and method for graft preparation and/or tissue repair employing a continuous loop of suture attached to a free floating needle. The free floating needle is not swaged on the suture so that, after passing the suture loop construct through the graft or the tissue to be treated, the needle may be recentered if the suture strands are uneven.

The present invention also provides a method of forming a suture loop/needle construct having increased strength by: (i) providing a continuous loop of suture; and (ii) attaching a free floating needle to the continuous loop of suture.

The invention also provides methods of threading suture through or around tissue (for example, a graft) employing a suture loop/needle construct. Methods for securing a first tissue to a second tissue that allows for accelerated tissue healing, by employing a suture loop/needle construct, are also provided.

These and other features and advantages of the invention will be more apparent from the following detailed description that is provided in connection with the accompanying drawing and illustrated exemplary embodiments of the invention.

BRIEF DESCRIPTION OF THE DRAWINGS

FIG. 1 illustrates a construct in accordance with the present invention, the construct having a continuous loop of suture attached to a free floating needle;

DETAILED DESCRIPTION OF THE PREFERRED EMBODIMENTS

The present invention provides a suture loop/needle construct with increased strength and a method of employing such suture loop/needle construct in surgery (for example, arthroscopic surgery). The suture loop/needle construct of the present invention may be employed for threading suture through or around a first tissue (for example, a graft) with maximum suture fixation strength.

Additionally, and if desired, the first tissue may be further secured to a second tissue that allows for accelerated healing. In exemplary embodiments, the first tissue may comprise at least one of (i) biological tissue, such as soft tissue (for example, tendon, ligament, graft, or combination thereof) or hard tissue (for example, bone); and/or (ii) non-biological tissue. The second tissue may also comprise at least one of (i) biological tissue, such as soft tissue (for example, tendon, ligament, graft, or combination thereof) or hard tissue (for example, bone); and/or (ii) non-biological tissue. The second tissue may comprise tissue that is similar to or different from the first tissue. For example, the first tissue may be a portion of a torn ligament, while the second tissue may be bone, or a different portion of the same torn ligament, or a non-biological tissue construct such as a fixation device.

Figure 2:
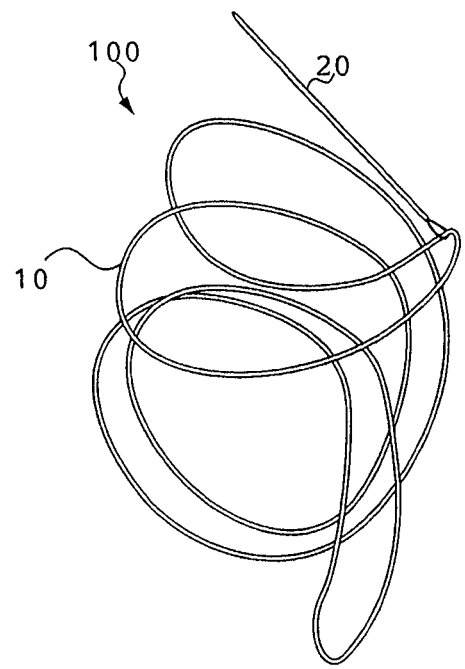
FIG. 2 illustrates another view of the suture loop/needle construct of FIG. 1.

Referring now to the drawings, where like elements are designated by like reference numerals, FIGS. 1 and 2 illustrate a suture/needle construct 100 formed according to a method of the present invention. In an exemplary embodiment, suture/needle construct 100 comprises at least one continuous loop of suture 10 (preferably a continuous loop of #2 FiberWire suture 1 (as described below) that is attached to a free floating needle 20.

The continuous loop of suture 10 of the present invention may be formed of any flexible material. In the preferred embodiment, the continuous loop is formed of a high strength suture material such as Arthrex FIBERWIRE suture, which is described in U.S. Pat. No. 6,716,234 to Grafton et al., the disclosure of which is incorporated by reference in its entirety. FIBERWIRE suture is formed of an advanced, high-strength fiber material, namely ultrahigh molecular weight polyethylene (UHMWPE), sold under the tradenames SPECTRA (Honeywell) and DYNEEMA (DSM), braided with at least one other fiber, natural or synthetic, to form lengths of suture material. The FIBERWIRE suture may include a core within a hollow braided construct, the core being a twisted yarn of UHMWPE. The suture may optionally include filaments of various colors.

Although the invention is described with reference to a single continuous loop of high strength suture 10 that is attached to needle 20, the invention is not limited to this embodiment and encompasses embodiments where a plurality of continuous loops of suture 10 (which may comprise at least one continuous loop of high strength suture) are attached to needle 20. Each suture loop of the plurality of suture loops may be attached individually to the needle 20. The perimeter of each suture loop is preferably fixed and the suture loops may have similar dimensions.

In a preferred embodiment, free floating needle 20 is a very thin metal needle (preferably nitinol or stainless steel) that allows an increased number of suture loop passes through or around the tissue to be sutured or attached, with decreased trauma. The free floating needle 20 is not swaged on the suture loop 10 so that, after passing the suture loop 10 through the tissue to be treated, needle 20 may be recentered if the suture strands are uneven. In this manner, the tissue to be treated is maintained intact and, in turn, a stronger tissue/suture construct is formed. In addition, as the free floating needle 20 is not swaged, it can be manufactured much thinner (about 1 to about 3 mm diameter, more preferably of about 2 mm diameter) than the conventional swaged on needles. A thinner needle is much less traumatic, keeping tissue intact and allowing an increased number of passes through tissue.

Free floating needle 20 may be attached directly or indirectly to the suture loop 10 (or, as noted above, to a plurality of suture loops). For example, and as shown in FIG. 1, needle 20 may be attached to the suture loop 10 through an eyelet or loop 22, which may be formed integral to the needle 20 (during manufacturing) or attached to the needle 20 after the formation of the needle. Loop 22 may have various shapes and may be formed of various materials (for example, nitinol or suture, preferably a high strength suture material) and may have various dimensions that allow the needle 20 to freely move around the perimeter of suture loop 10. Needle 20 need not be straight and may have various shapes or configurations (for example, curved, or a combination of straight and curved), depending on the characteristics of the surgical procedure involved.

The suture/needle construct 100 may be provided with free floating needle 20 having a first length $L_1$ and suture loop 10 having a second length $L_2$, which may be similar to or different from the first length $L_1$ of the needle 20. For example, and as illustrated in FIG. 1, needle 20 may have a length $L_1$ of about 3 cm (for a needle with a diameter of about 3 mm), whereas the length $L_2$ of the suture loop may be of about 5 cm (for a suture with a diameter of about 2.5 mm).

In yet additional embodiments, the suture loop/needle construct of the present invention may be provided with a free floating needle 20 attached to a chain of suture loops, preferably of braided high strength suture loops, for surgical applications, such as disclosed in U.S. Pat. Publication No. 2007/0135843, the disclosure of which is incorporated by reference. As disclosed in the published application, the suture chain can comprise a series of closed loops of suture formed in a conventional "chain." Alternatively, at least one of the loops or "links" of the chain can be formed first by "piercing" or "lacing" an end of the suture through a standing part of the suture, to form an initial suture "intersection" in a first direction (for example, in the x-y direction). The suture intersection is then locked by lacing the end through the suture intersection in a second direction (for example, in the z direction), piercing both strands at the center of the initial junction, and pulling the strands tight. Successive loops or links may be developed along the length of suture in similar fashion to form a suture chain.

The loops of the chain can be, but need not be, interlinked, and the chains of the present invention can include two or more loops that are connected together. Each loop preferably has a fixed perimeter. All loops may be similar in size.

In an exemplary embodiment only, at least one (preferably all) of the loops of the chain may be formed of high-strength suture such as FIBERWIRE suture. The suture loops of the suture chain may also comprise suture that may optionally include filaments of various colors.

The method of threading suture through or around tissue of the present invention will be described below with reference to a particular exemplary embodiment. In this particular exemplary embodiment, the tissue to be treated is a soft tissue graft prepared for tissue fixation by stitching the graft, for example, with the suture loop/needle construct 100 of the present invention. In additional exemplary embodiments, single tendon strands may be sutured together by passing the suture loop/needle construct 100 of the present invention over the graft. Although the invention will be described with reference to particular exemplary embodiments, it must be understood that the invention is not limited to these embodiments and contemplates treatment (such as suturing or attachment, for example) of any tissue with the suture loop/needle construct 100 described above.

FIGS. 3-9 illustrate an exemplary method of stitching a soft tissue graft comprising single tendon strands that are sutured together by passing the suture loop/needle construct 100 of the present invention over the graft. The suture loop/needle construct 100 may be passed over a free end of the graft tendons, with the needle 20 being passed through the graft tendons at a starting point (which, in an exemplary embodiment, is located at about the center of the graft tendons). At described below, the graft tendons may be stitched together starting from the center and moving toward the end of the graft.

Figure 3:
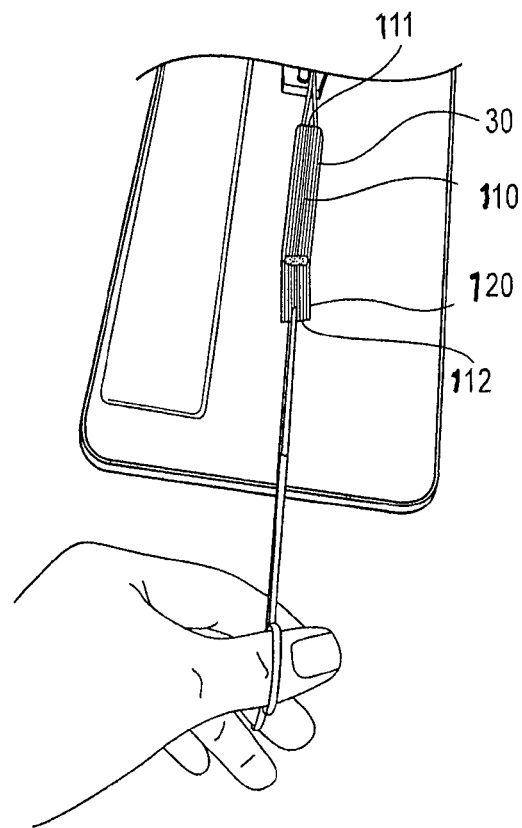
FIG. 3 illustrates a processing step for preparing a whip stitched graft construct in accordance with an embodiment of the present invention, and employing the suture loop/needle construct of FIG. 1.

FIG. 3 illustrates a working station with a preparation area having a soft tissue graft comprising single tendon strand 30 folded in half at end 111 of the preparation area, so that regions 110, 120 of the tendon strand are securely affixed to the end 111. As shown in FIG. 3, opposite ends 112 of the graft tendon regions are held by hand and/or by employing a clamp, for example. Alternatively, the opposite ends 112 of the graft can be also affixed to the preparation area but in a way that allows the graft to be easily released to pass a suture loop over the graft.

Subsequent to the graft fixation at the work station, a flexible strand is provided in the vicinity of the preparation area and of the graft. According to an exemplary embodiment of the invention, the flexible strand may be strand 10 of the suture loop/needle construct 100 (preferably a continuous loop of #2 FiberWire suture attached to free floating thin needle 20).

The thin needle is preferably straight and easy to handle, without instruments. The needle moves freely on the suture 10 to recenter itself after passing through tissue and to facilitate even tensioning. As shown in detail in FIG. 2, the free floating needle 20 is not swaged on the suture 10 so, after passing the suture loop construct 100 through the tissue to be treated, the needle 20 may be recentered if the suture strands are uneven.

Figure 5:
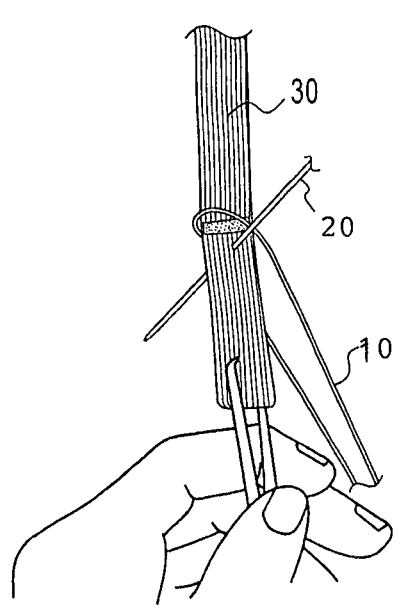
FIG. 5 illustrates a processing step for preparing the whip stitched graft construct of the present invention, and at subsequent step to that shown in FIG. 4.
Figure 4:
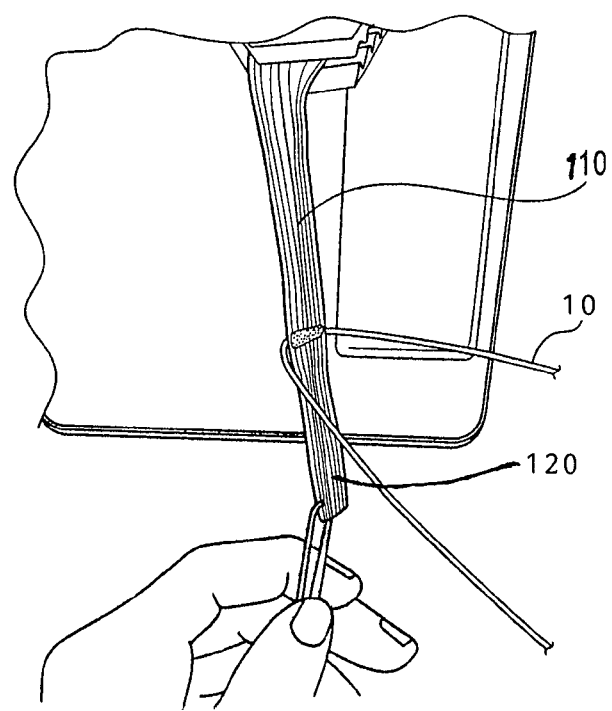
FIG. 4 illustrates a processing step for preparing the whip stitched graft construct of the present invention, and at subsequent step to that shown in FIG. 3.

Flexible suture loop 10 attached to free needle 20 is passed over the free ends 112 of the graft tendon, as shown in FIG. 4. The needle is then passed through the graft tendon regions 110, 120 at a proximal starting point which, in an exemplary embodiment only, is located at about the center of the graft tendon regions (FIG. 5). As described below, the graft tendon regions will be stitched together starting from the center and moving toward the ends 112 of the graft.

Figure 6:
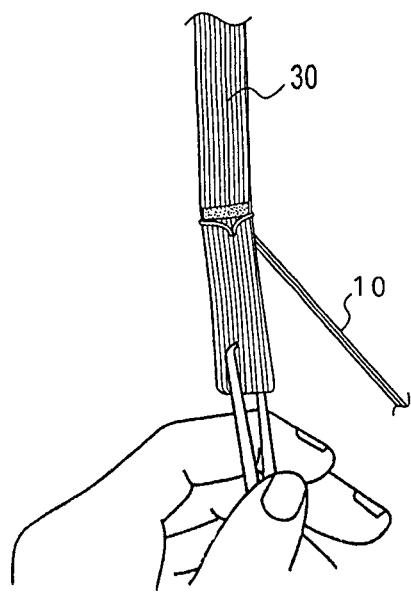
FIG. 6 illustrates a processing step for preparing the whip stitched graft construct of the present invention, and at subsequent step to that shown in FIG. 5.
Figure 7:
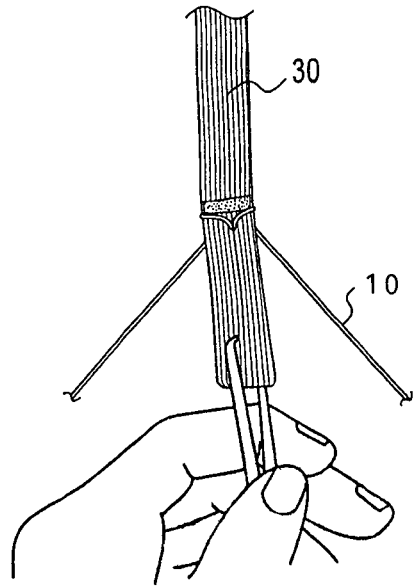
FIG. 7 illustrates a processing step for preparing the whip stitched graft construct of the present invention, and at subsequent step to that shown in FIG. 6.
Figure 8:
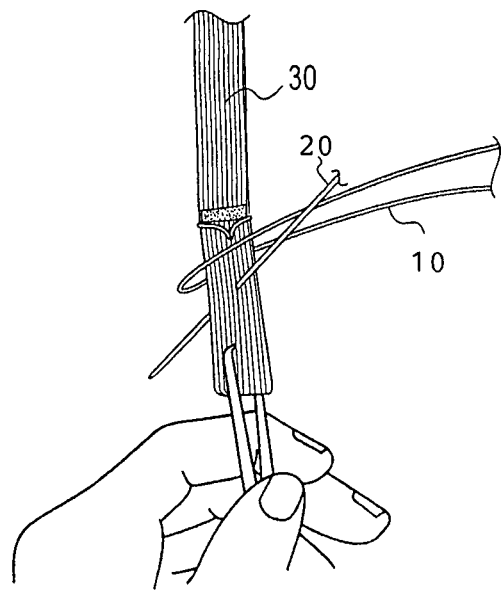
FIG. 8 illustrates a processing step for preparing the whip stitched graft construct of the present invention, and at subsequent step to that shown in FIG. 7.
Figure 9:
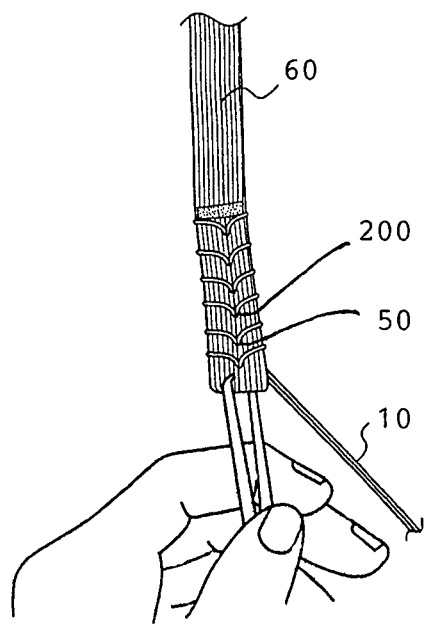
FIG. 9 illustrates a processing step for preparing the whip stitched graft construct of the present invention, and at subsequent step to that shown in FIG. 8.

Referring now to FIGS. 6 and 7, after passing and tensioning the first stitch, the suture strands are spread on either side of the graft, dropping the graft between the strands. The needle 20 is then passed through the graft tendon regions, distal to the first pass (i.e., towards the ends 112 of the graft tendon regions), as shown in FIG. 8. Preferably, the needle 20 is inserted on the same side of the graft with each pass.

This process is repeated until a desired stitching length is obtained. For example, the graft formed according to an exemplary embodiment of the present invention may be provided with a first stitched region 50 (FIG. 9) of the graft (comprising single tendon strands sutured together) which is adjacent a second region 60 of the graft (comprising segments of the single tendon strands that are not tied together).

Subsequent to the stitching operation, needle 20 may be cut off and the suture loop maintained or, alternatively, cut more proximal to give two free ends of suture. If a last minute length change to the stitched area of the graft is needed, then the distal passes of suture may be unthreaded and the graft cut to size.

Stitched tissue (for example, stitched tissue graft such as tendon graft) prepared according to embodiments of the present invention (i.e., employing the suture loop/needle construct 100) may be used for reattachment or fixation with a fixation device (such as an interference screw, for example) for ligament reconstruction. Suture loop/needle construct 100 is employed to simply put stitches in the graft and prepare the stitched or sutured graft for further surgical procedures (for example, ligament reconstruction and fixation to a fixation device such as interference screw).

Although the present invention has been described above with reference to a particular exemplary embodiment (i.e., suturing a soft tissue graft or a plurality of single tendon strands by passing the suture loop/needle construct 100), the invention is not limited to this particular embodiment and contemplates treatment of any tissue (for example, suturing or attachment of biological tissue like cartilage, tendon, etc.) with the suture loop/needle construct 100; and/or treatment of a first tissue (for example, bone, tendon, ligament, fixation device, etc.) relative to a second tissue (for example, bone, tendon, ligament, fixation device, etc.), the first tissue being similar to, or different from, the second tissue. Thus, the present invention contemplates tissue repairs, such as ligament repair, i.e., simple suturing of tissue, tendon to tendon repair, graft to bone repair, or tendon to bone repair, among others, with the suture loop/needle construct 100 of the present invention.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method of stitching a soft tissue graft tendon comprising a plurality of single tendon strands by threading suture through or around the graft tendon to prepare the graft tendon for fixation in a ligament reconstruction procedure, comprising the steps of:

providing a suture loop/needle construct in the vicinity of a graft tendon, the suture loop/needle construct comprising a continuous suture loop formed by lacing an end of the suture through a standing part of the suture and a free floating needle including an eyelet, the free floating needle being attached to the continuous suture loop through the eyelet, the eyelet being configured to allow the free floating needle to freely move around a perimeter of the continuous suture loop and to recenter itself on the continuous suture loop;

passing the suture loop/needle construct through the graft tendon at a first location to form a first stitch;

after being passed through the graft tendon at the first location, the free floating needle recentering itself on the continuous suture loop to facilitate even tensioning;

passing the suture loop/needle construct through or around the graft tendon at a second location to form a second stitch, the second location being different from the first location;

repeating the above stitching process multiple times until a stitched portion with a desired stitching length is obtained on the graft tendon; and fixing the stitched graft tendon during a ligament reconstruction procedure using a fixation device and fixating the stitched graft tendon to the fixation device.

2. The method of claim 1, wherein the free floating needle is a nitinol needle with a diameter of about 2 mm.

\* \* \* \* \*